United States Patent [19]

Barthe et al.

[11] Patent Number: 4,765,888
[45] Date of Patent: Aug. 23, 1988

[54] ARTIFICIAL KIDNEY WITH INTEGRATED DIALYSATE CIRCUIT

[75] Inventors: Bernard Barthe, Bretigny sur Orge; Georges Vantard, Gournay sur Marne; Jean-Pierre Vasseur, Longjumeau, all of France

[73] Assignee: Hospal Industrie, Meyzieu, France

[21] Appl. No.: 790,575

[22] Filed: Oct. 23, 1985

Related U.S. Application Data

[63] Continuation of Ser. No. 653,963, Sep. 24, 1984, abandoned, which is a continuation of Ser. No. 512,915, Jul. 12, 1983, abandoned, which is a continuation of Ser. No. 314,734, Oct. 26, 1981, abandoned.

[30] Foreign Application Priority Data

Nov. 13, 1980 [FR] France .................................. 80 24476

[51] Int. Cl.[4] .............................................. B01D 13/00
[52] U.S. Cl. ........................................ 210/86; 210/90; 210/136; 210/321.65
[58] Field of Search ............... 210/86, 87, 90, 96.2, 210/128, 129, 136, 257.2, 258, 321.1, 321.2, 321.3, 321.4, 321.5, 416.1, 321.65; 653/963

[56] References Cited

U.S. PATENT DOCUMENTS

| | | | |
|---|---|---|---|
| 3,774,762 | 11/1973 | Lichtenstein | 210/94 |
| 3,912,455 | 10/1975 | Lichtenstein | 422/61 |
| 3,946,731 | 3/1976 | Lichtenstein | 210/87 X |
| 4,024,059 | 5/1977 | Sausse | 210/257.2 X |
| 4,191,646 | 3/1980 | Larsson et al. | 210/321.3 X |
| 4,366,051 | 12/1982 | Fischel | 210/96.2 |
| 4,370,983 | 2/1983 | Lichtenstein | 210/321.2 X |

Primary Examiner—Frank Spear
Attorney, Agent, or Firm—Gerald D. Sharkin; Robert S. Honor; Walter F. Jewell

[57] ABSTRACT

An artificial kidney comprising a haemodialyser 16 connected to a dialysis liquid circuit. The latter can be entirely integrated, that is to say that the functions previously performed by a plurality of self-contained members connected to one another are now performed by a common unit consisting of a very small number of multifunctional components. This common unit is preferably disposable. A small console groups together, with their electric circuits, the re-usable means for controlling and checking the artificial kidney.

15 Claims, 10 Drawing Sheets

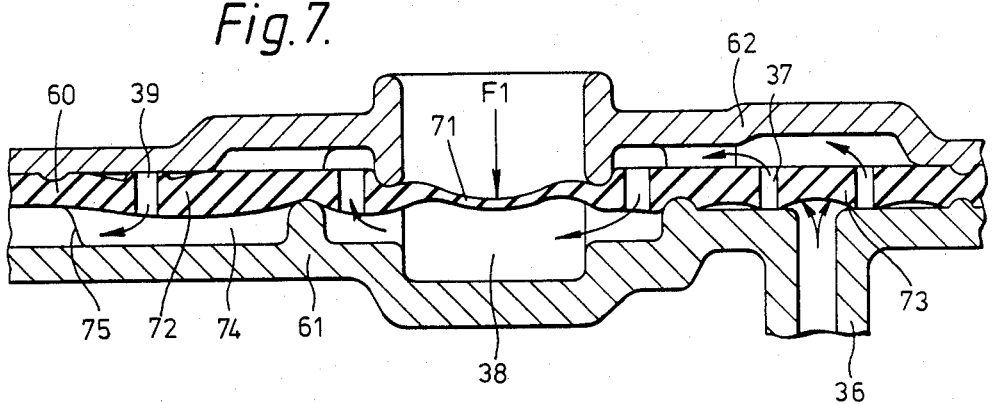
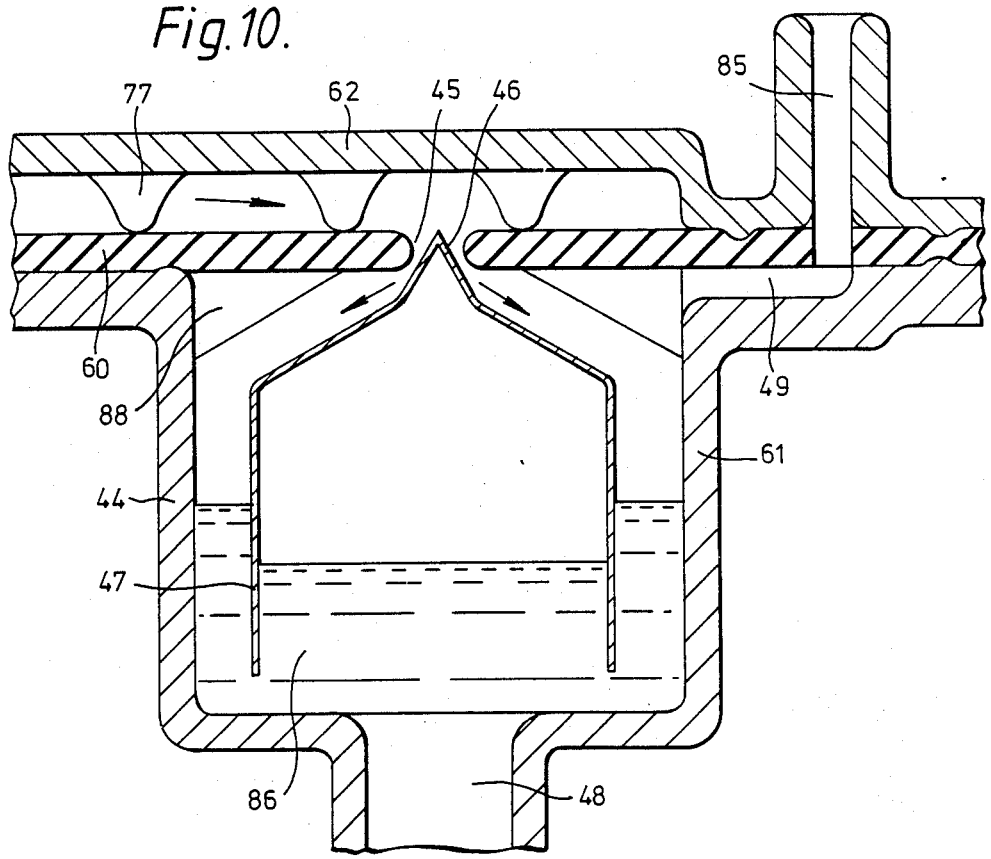

ARTIFICIAL KIDNEY WITH INTEGRATED DIALYSATE CIRCUIT

This application is a continuation of application Ser. No. 653,963 filed Sept. 24, 1984, now abandoned, which, in turn, is a continuation of application Ser. No. 512,915, filed July 12, 1983, now abandoned, which in turn, is a continuation of application Ser. No. 314,734, filed Oct. 26, 1984, now abandoned.

DESCRIPTION

The present invention relates to an artificial kidney.

The artificial kidneys in current use comprise a disposable haemodialyser and elements constituting a circuit through which the blood passes, these also being disposable. For the purpose of simplifying the manufacture of these devices, reducing their cost and facilitating their use, it has been proposed to incorporate, into the haemodialyser, certain elements of the circuit through which the blood passes, thus forming a single disposable unit around the haemodialyser, to which, in addition to a few accessories, the elements constituting the circuit through which the dialysis liquid passes, which elements can generally be re-used after sterilisation, can be connected during use.

Still with the same purpose of simplification and cost reduction, it has recently been proposed to associate, with each haemodialyser, a set of pre-assembled disposable elements constituting all or part of the circuit through which the dialysis liquid passes, and disposable elements making it possible to remove and measure the desired amounts of ultrafiltrate. Thus, an artificial kidney is available which consists essentially of a plurality of disposable self-contained elements which each perform a particular function and which are connected to one another.

Artificial kidneys of this type represent a real improvement over the artificial kidneys of the prior art, but there still remains the need to have constantly available artificial kidneys which are more economical, both as regards manufacture and as regards assembly, transportation or use, and which are easier to use and more reliable.

According to the present invention there is provided an artificial kidney comprising:
(a) a haemodialyser including:
  (i) a casing separated into first and second compartments;
  (ii) first connections for introducing and removing blood to and from said haemodialyser mounted on said first compartment;
  (iii) second connections for introducing and removing dialysis liquid to and from said haemodialyser mounted on said second compartment;
  (iv) a membrane enabling the blood to be treated by dialysis and by ultrafiltration;
(b) blood circulation means external to said haemodialyser and connected to said first connections to circulate blood through said first compartment;
(c) a common unit which is at least partly integrated (as herein defined) providing means external to said haemodialyser for preparing the dialysis liquid, said common unit being connected to said second connections and including means to circulate the dialysis liquid through said second compartment;
(d) means for storing the dialysis liquid when fresh and/or used;
(e) means for removing and measuring amounts of used dialysis liquid equal to the desired amount of ultrafiltrate; and
(f) means for controlling and checking the blood circulation means and dialysis circulation means.

Such an artificial kidney may be of compact simplified construction, which involves fewer components and less material and is hence substantially more economical. It can have low weight and low bulk, which makes it easier to transport, store and use. Furthermore it can be rapid, safe, simple and economical to use.

The present invention is not based on an attempt to find the best possible way of assembling all the components required to carry out the desired functions, but, on the contrary, is based on an attempt to reduce the number of self-contained members by incorporating different members, each having at least one particular function, into a common unit.

According to the invention, this problem is solved by at least partial integration of the means for preparing the dialysis liquid and circulating it inside and outside the haemodialyser. The term "integrated" is understood here as meaning a construction which has multifunctional elements which are common to at least two different members and which have a particular function in each of these members. These functions can be either of the same type or of a different type.

The term "totally integrated" is understood as meaning a unit grouping together various members consisting exclusively of multifunctional elements.

The term "partially integrated" is understood as meaning either a unit consisting of members of which only some have one or more multifunctional elements in common, or a unit consisting of members which only partially consist of multifunctional elements, or also a unit consisting of a combination of the previous two cases.

Furthermore, as the haemodialysers have hitherto benefitted from numerous and significant improvements brought about by mass production, and since the equipment, the function of which is in particular to prepare the dialysis liquid, store it and cause it to circulate, and to check the ultrafiltrate, has only developed, by contrast, to a relatively small extent, a substantial technological imbalance has resulted. The present invention thus proposes to transfer the greatest possible number of elements of this equipment to a disposable unit, most frequently constructed around the haemodialyser, so that they benefit from mass-production technology.

It will become clearly apparent from the description which now follows that, since the dialysis circuit of an artificial kidney consists of a plurality of members each ensuring very particular functions, the integration of two or more of these members into a common unit can lend itself to a multiplicity of solutions, firstly because of the type and number of the integrated members and secondly because of the choice of the technological solution selected for carrying out this integration.

In order that the present invention will be more fully understood, the following description is given, merely by way of example, reference being made to the accompanying drawings, in which:

FIG. 7 is a section, taken along an axial plane, of the membrane pump of the kidney;

FIG. 10 is a view similar to FIG. 8 showing a modified embodiment of the float-type device.

Figure 1:
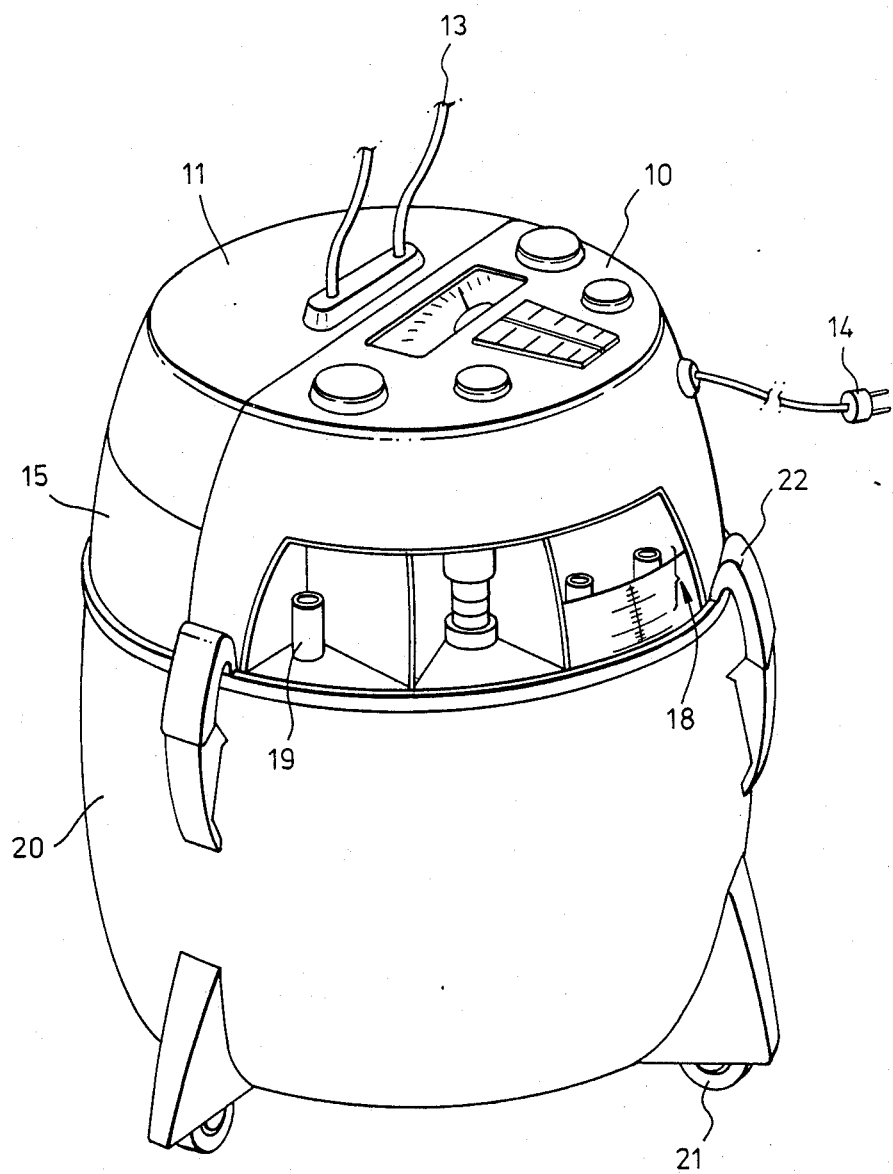
FIG. 1 is a perspective view of a presently preferred embodiment of artificial kidney according to the present invention.
Figure 2:
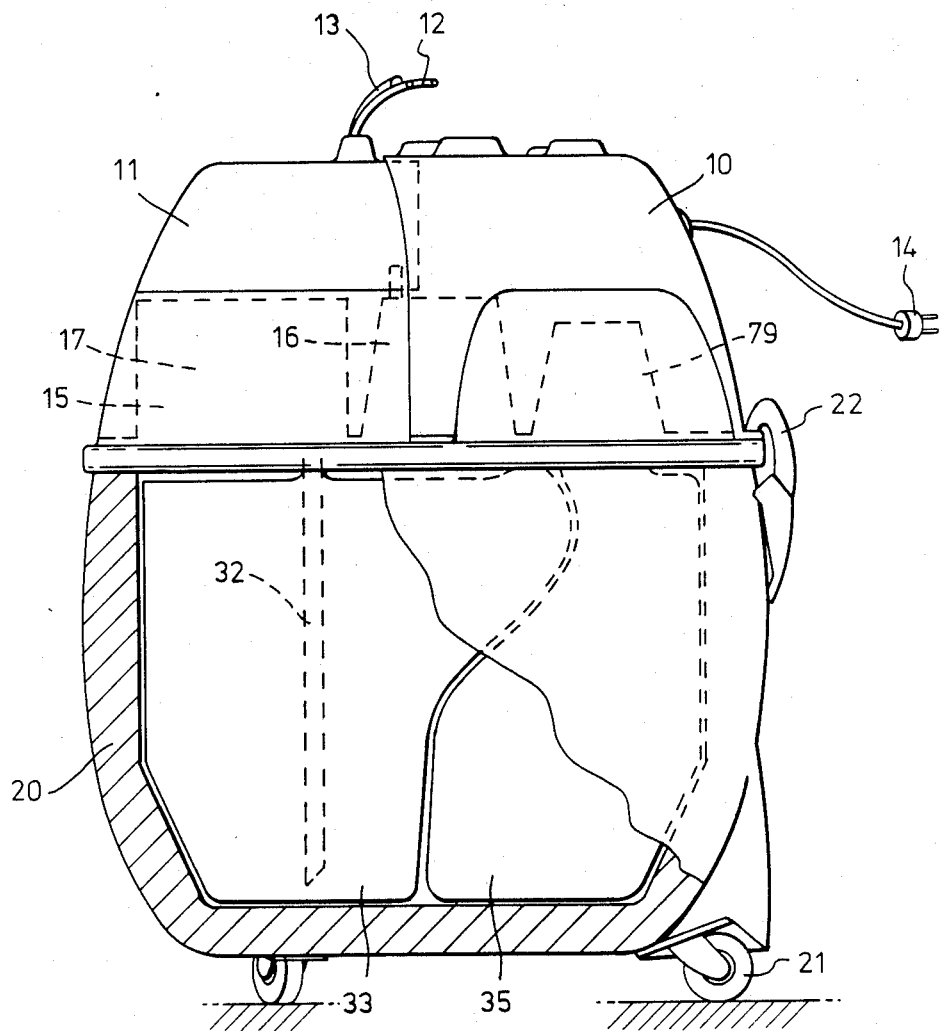
FIG. 2 is a side view, partly in section, of the artificial kidney of FIG. 1.

The artificial kidney shown in FIGS. 1 and 2 can be subdivided into three zones of different levels. The upper zone comprises a console 10 grouping together the members for controlling and checking the artificial kidney, and, under a suitable fairing 11, the means outside the haemodialyser for causing the blood to circulate. The blood circulation tubes 12 and 13 connect the artificial kidney to the patient; the console can be connected to an electricity supply by means of the plug 14.

In the intermediate zone 15, means 17 for preparing the dialysis liquid, means for causing it to circulate, and means 18 for removing and measuring amounts of liquid equal to the desired amounts of ultrafiltrate, are grouped together around a haemodialyser 16. The means 17 can be connected by an adaptor 19 to a supply of running water which has been heated and softened beforehand.

The lower zone consists of a container 20 intended for containing and delimiting the volume of dialysis liquid required for a session. This container is non-deformable under the usual stresses and its walls are preferably made of a thermally insulating material in order to keep the dialysis liquid at a temperature similar to that of blood during the session. Advantageously, it can be mounted on wheels 21 and it can be provided with quick-action lever fasteners 22 for holding the main elements of the artificial kidney together during the haemodialysis session.

When carrying out treatments according to relatively moderate purification levels defined, for example, by a weekly clearance of 70 to 90 liters of urea and 20 to 30 liters of vitamin $B_{12}$, it is possible to reduce the total volume of dialysis liquid required for a session from about 200-300 liters to less than 50 liters, for example to 30 liters.

According to the invention, it is also possible, by virtue of the integration of various members of the dialysis liquid circuit into a common unit, to reduce the volume of the equipment to less than about ten litres, so that, in total, the volume of the whole of the artificial kidney, together with the dialysis liquid required for a session, does not exceed about 40 liters, as compared with about 400 liters for conventional artificial kidneys. This is a considerable advantage for transportation, storage and use.

Figure 3:
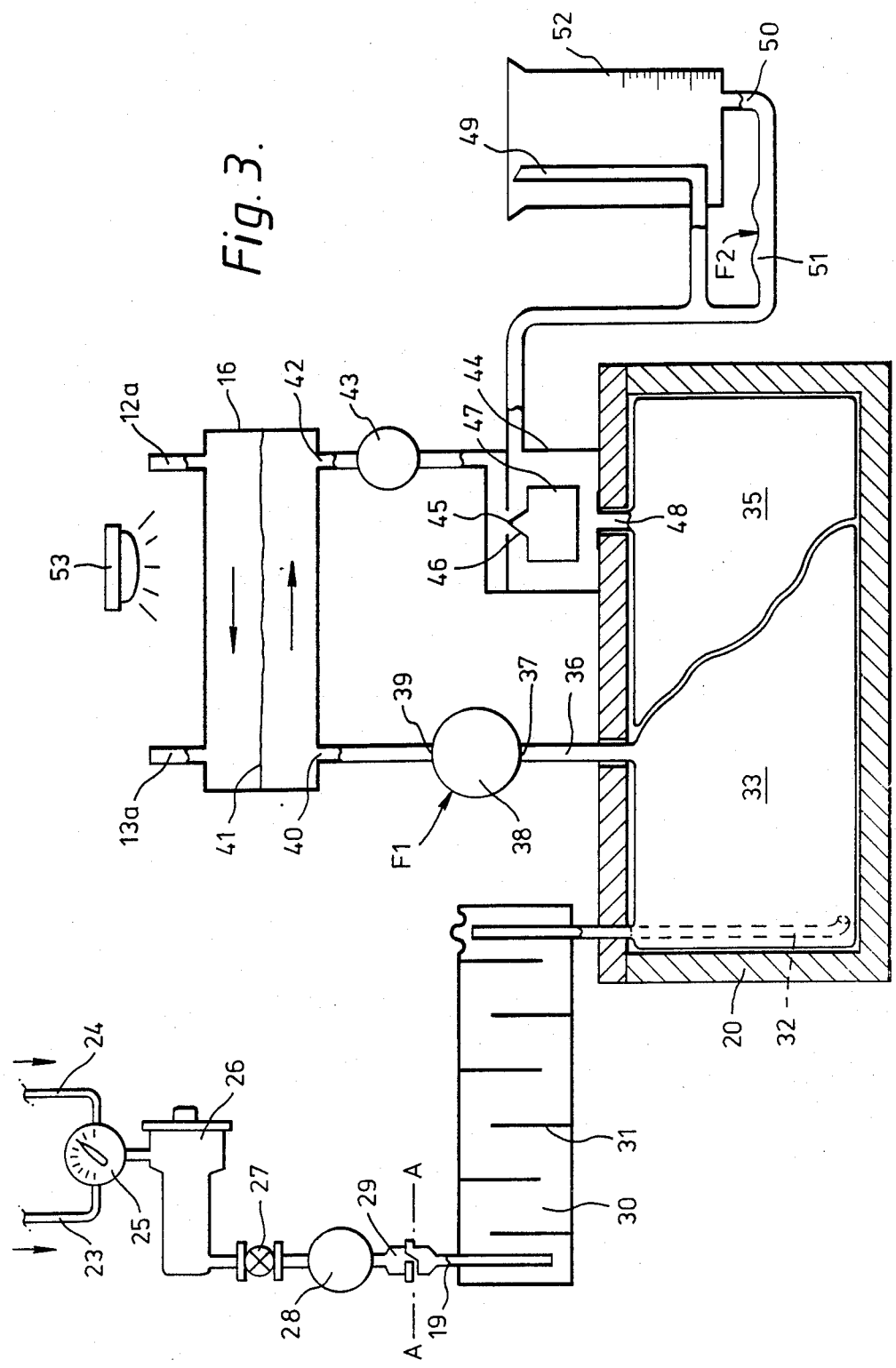
FIG. 3 is a diagram illustrating schematically the means for preparing the dialysis liquid, storing it and causing it to circulate, through the artificial kidney.

FIG. 3 shows members necessary for the preparation, the storage and the circulation of the dialysis liquid in the artificial kidney and their main connections. Some of these members, located, for example, upstream of the dot-and-dash line AA indicating the middle of a connector 29, can be permanently installed and be re-used for each haemodialysis session. According to the invention, the members arranged downstream of this connector are at least partially integrated in order to form a common unit. Advantageously, preferably almost all the members arranged downstream of this connector can be disposable.

The circuit for dispensing running water comprises a cold water inlet 23 and a hot water inlet 24. A mixing device 25, equipped with a thermostat of a commercially available type, makes it possible to provide water at a desired temperature between 37° C. and 40° C.

If appropriate, this water passes through a softening device 26 provided, for example, with ion exchange resins of types known per se, which can be regenerated periodically. The softened water then passes through a manually controlled tap 27 and an automatic valve 28, the closure of which is governed by a pressure controller limiting the pressure of the water downstream to a pre-set value of the order of 100 mm of mercury.

A quick-action connector 29 of a type known per se makes it possible to connect the re-usable upstream members to the downstream members, which are most frequently disposable.

This quick-action connector 29 is connected via an adaptor 19, to a reservoir 30 which preferably initially contains a concentrated solution of dialysis liquid. The volume of this reservoir is determined so that it contains the necessary amount of concentrate in advance, this amount corresponding exactly to the dialysis liquid capacity of the circuit. A volume of concentrated solution of about 1 liter, which must be defined with a precision of ±25 ml, corresponds to a dialysis liquid capacity of 30 liters. The reservoir 30 is advantageously equipped with baffles 31 which facilitate the displacement of the concentrated solution water entering through the adaptor 19.

A dip tube 32 connects the upper part of the reservoir 30 to the bottom of the container 20. Advantageously, the water and the dialysis concentrate are collected inside the first of two compartments 33, 35 of a leaktight, deformable, supple plastic bag which is initially devoid of air and is capable of occupying a volume equal to the internal volume of the container 20.

The container 20 is closed by a cover 34 through which pipes, including the dip tube 32, pass. The compartment 33 of the bag can be closed around the dip tube 32, for example by heat-sealing it to the underside of the cover. The bag is also connected in a leaktight manner to a tube 36 connected to an intake orifice 37 of a pump 38.

This pump can be of the membrane type and be actuated, in the direction of the arrow $F_1$, by any device of a type known per se (not shown), such as a cam controlled by an electric motor.

The delivery orifice 39 of pump 38 is connected to an inlet orifice 40 of the haemodialyser 16. The latter is separated by a membrane 41 into two compartments, namely a first compartment through which the blood passes between the orifices 12a and 13a to which the tubes 12 and 13 are connected, and a second compartment through which the dialysis liquid passes, generally in countercurrent to the blood, between the inlet orifices 40 and an outlet orifice 42.

If appropriate, a heating device 53, for example of the infra-red radiation type, which is integral with the console 10, keeps the temperature of the blood within the desired range at the outlet of the haemodialyser.

The outlet orifice 42 of the haemodialyser is connected to a transparent tube element 43 cooperating with a colorimeter of a type known per se (not shown), which is housed in the console 10. This element 43 is connected to a float chamber 44 provided in its upper part with an orifice 45 forming the seat of the needle-valve 46 of a float 47, which can move inside the chamber 44. The bottom of the chamber 44 opens directly into the container 20, via an orifice 48. The chamber 44 is open to the atmosphere via a tube 49.

The used dialysis liquid can accumulate in the container 20, inside the compartment 35 of the supple bag, which is similar to the compartment 33 and complementary thereto.

The blocking device consisting of the needle-valve integral with the float, moving opposite its seat 45, automatically regulates the pressure of the dialysis liquid in the haemodialyser, at all times, to values between atmospheric pressure and the pressure of the blood.

The means for removing and measuring amounts of liquid (by volume, by weight and/or by flow rate) equal to the desired amounts of ultrafiltrate consist of a tube 50 equipped with a supple section 51 capable of being closed by an external device of any known type, such as an adjustable screw, which acts in the direction of the arrow $F_2$ in order to block the section of the tube 50 to a greater or lesser extent. This tube 50 opens out in a graduated receiver 52. Advantageously, the tube 49 also opens out in the receiver 52. The volume of liquid withdrawn is immediately replaced by an equal volume of ultrafiltrate passing through the membrane, until the pressure of the dialysis liquid in the haemodialyser has been restored to its initial value. Thus, the artificial kidney according to the invention preferably checks the ultrafiltrate by a volumetric method.

According to a particular embodiment of the invention, it has been found that the following members can be integrated into a common unit:
  the tank 30 initially containing a calibrated amount of concentrated solution of dialysis liquid,
  the pump 38,
  the haemodialyser 16,
  the transparent tube 43,
  the chamber 44 and its float 47, and
  the graduated receiver 52, the tubes 49 and 50 and the closure device 51.

This common unit can be connected on the one hand, by the connector 29, to a source of water heated and softened beforehand, and on the other hand to a container 20 for storing the exact volume of dialysis liquid necessary for a haemodialysis session. Preferably, the container 20 is itself integrated into the common unit defined above.

It has been found that various components of the haemodialyser, such as a sealing gasket and holding components, can advantageously be made multifunctional.

This integration is not a simple juxtaposition of known members of which the connecting elements have been shortened or the connections simplified. It is the creation of a novel common unit which, with the aid of a very small number of elements, makes it possible to carry out all the functions which each of the abovementioned members can perform independently.

Figure 4:
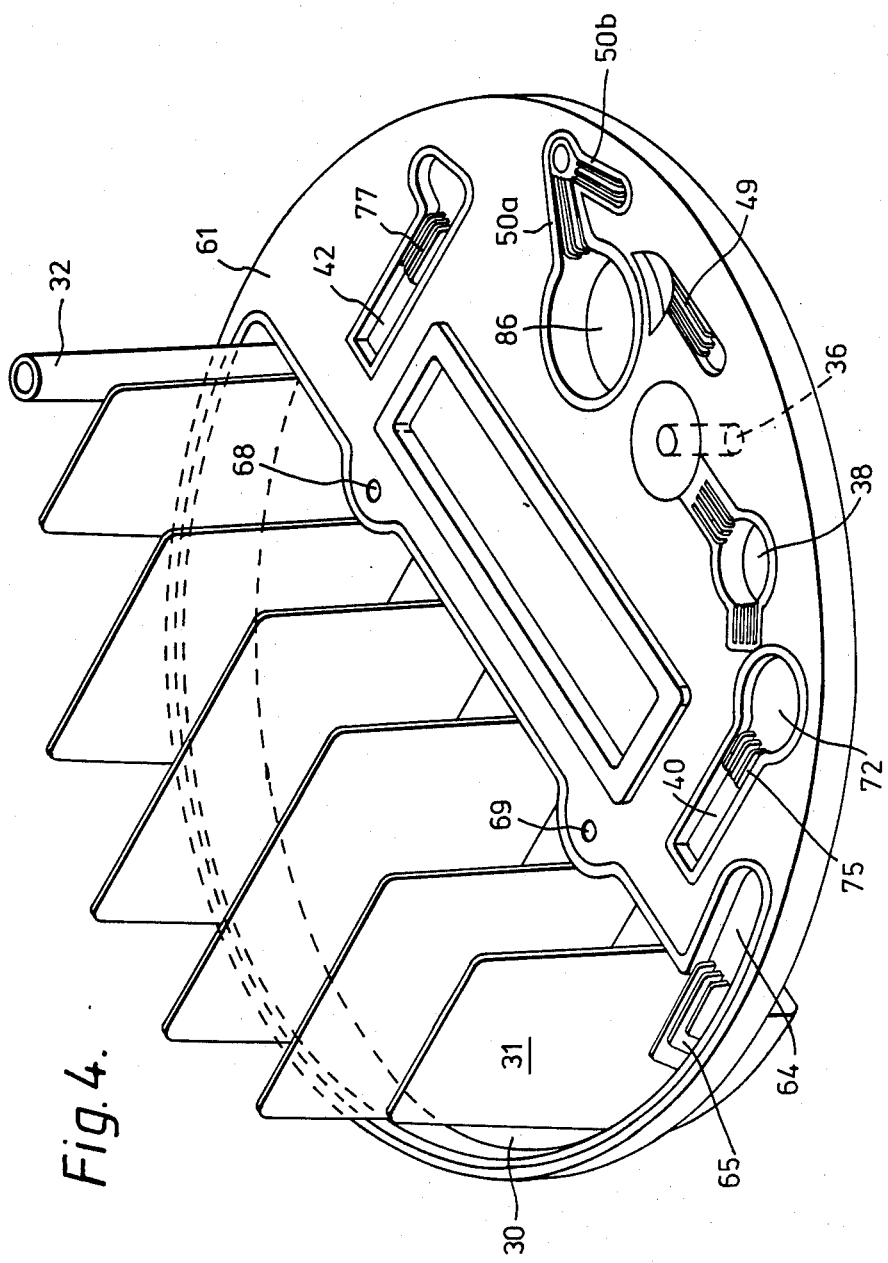
FIG. 4 is a perspective view of the lower component of the common unit, which groups together, around the haemodialyser, the means for preparing the dialysis liquid and causing it to circulate, and for removing amounts of liquid equal to the desired amounts of ultrafiltrate.
Figure 5:
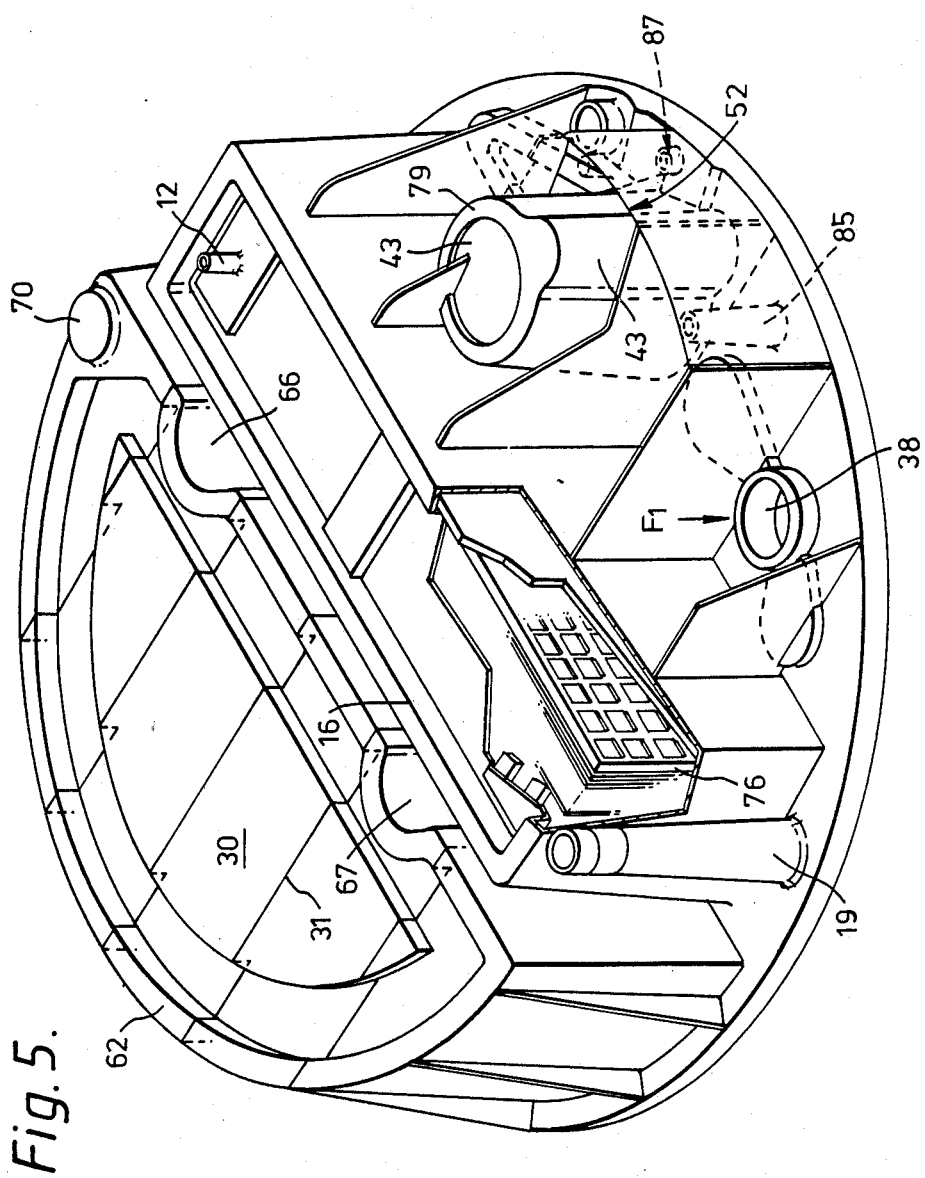
FIG. 5 is a perspective view of the upper component of the said common unit, with part broken away to illustrate the interior.
Figure 6:
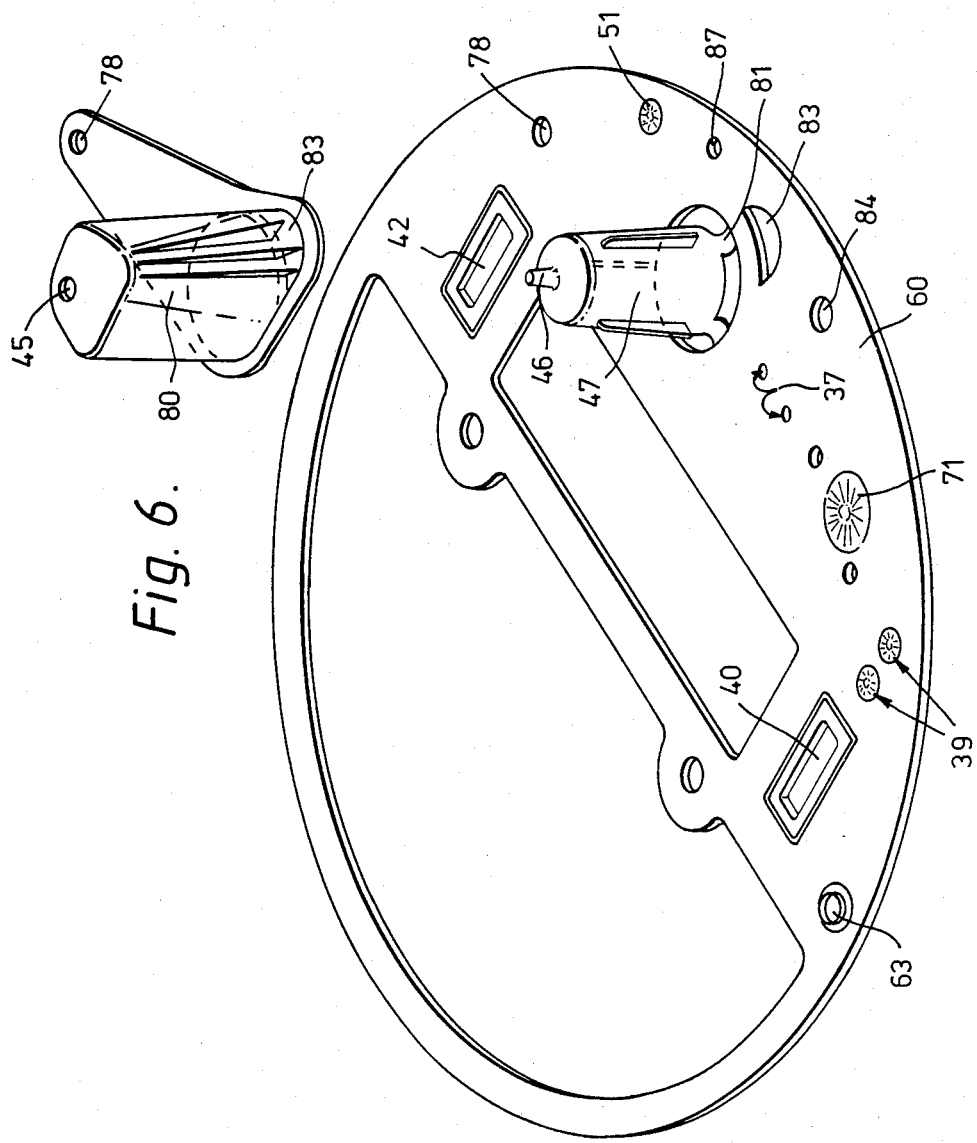
FIG. 6 is a perspective view of the intermediate component of the said common unit and of an attached part.

It has also been found that all these functions can preferably be performed essentially with the aid of a substantially plane, flexible and supple element 60 of low thickness, shown in FIG. 6, which is held clamped between two rigid or semi-rigid elements 61 and 62, shown respectively in FIGS. 4 and 5, the shapes of which are determined by the functions to be ensured. Each of these three elements is thus multifunctional. Thus, the supple element 60 has the essential function of ensuring leaktightness, in particular in contact with the dialysis liquid and in cooperation with the elements 61 and 62, but, locally, it has particular functions which will be indicated below.

With reference to FIG. 4, the lower element 61, which is preferably made of a rigid injectable plastic such as polyvinyl chloride or polyethylene, has the general shape of a perforated disc. If reference is made to FIGS. 4, 5 and 6, the adaptor 19 [FIG. 5], which is intended to be joined to the connector 29 and thereby to the fixed installation for dispensing water, is seen at the front. After the tank 30 has been filled with the solution of dialysis concentrate, this adaptor 19 can receive a stopper which had been replaced, before use, by a supple tube joined to the connector 29. The water passes through an orifice 63 in the element 60 [FIG. 6], which acts locally as a sealing gasket between the elements 61 and 62, and it then enters the reservoir 30 via the channel 64 [FIG. 4] formed by a recess in the upper surface of element 61 and provided with fins 65 for supporting the gasket 60.

The bottom of the reservoir 30 consists of about half of the disc 61. A first series of baffles 31 is integral with the bottom. The corresponding part of the upper element 62 [FIG. 5] constitutes the side walls, the cover and a second series of baffles of this reservoir. These baffles 31 are multifunctional because they also contribute to the rigidity of the unit. The elements 61 and 62 fit together exactly on either side of the semicircular sealing gasket consisting of the element 60. The generally diametral side wall of the reservoir on element 62 is provided with part-cylindrical recesses 66 and 67 [FIG. 5] to accommodate a clamping press which force-fits two pins, integral with the upper element 62, into corresponding cylindrical orifices 68 and 69 in the lower element 61. A portion of the dip tube 32 is integral with the lower element 61.

Advantageously, the upper element 62 [FIG. 5] comprises, above the upper orifice in the tube 32, a bistable boss 70 of thinned, rounded profile. Being pushed down during manufacture, this boss blocks the tube 32. In use, it is raised abruptly under the action of the pressure of the water which enters the reservoir 30, thus giving the dialysis liquid access to the container, via the tube 32.

The dialysis liquid stored in the compartment 33 of the supple bag is taken up by the pump 38, via the tube 36 [FIG. 4]. This pump, which is of the membrane type, is shown in greater detail in FIG. 7. The essential characteristic of this pump is the fact that the element 60 [FIG. 6] constitutes at one and the same time the membrane, the non-return check valve for the intake and delivery of the dialysis liquid, and the peripheral seal. This element 60 is located between the rigid elements 61 and 62, the shape of which is suitable for creating, between each of them and the membrane, the passages necessary for the dialysis liquid. Advantageously, these passages comprise ribs, such as 75 [see FIG. 4], for supporting the element 60. The displacement of the active part 71 of the membrane, which is suitably thinned and preformed, is obtained by an alternating action, in the direction of the arrow $F_1$, of any means integral with the console 10, such as a step-down motor driving a cam. The return of the active part of the membrane can be obtained either by the opposing action of a mechanical spring, or, preferably, by the elasticity of the membrane itself, or also by the fact that the membrane is locally rendered integral with the cam. When the active part 71 of the membrane moves in the direction of the arrow $F_1$, the dialysis liquid is driven downstream and pushes downwards the portion 72 of the membrane which constitutes the delivery check valve, thus freeing the delivery orifice 39. When the active part 71 of the membrane moves in the opposite direction to $F_1$, the pressure reduction created, in particular upstream, raises the portion 73 of the membrane which constitutes the inlet clack valve, thus permitting the introduction into the pump 38, via the orifices 37, of the dialysis liquid arriving through the tube 36.

The dialysis liquid thus passes through the channel 74, provided with ribs 75 for supporting the element 71, as far as the orifice 40 at the inlet of the haemodialyser 16.

This haemodialyser is of a type known per se, comprising a stack of intercalated plates 76, which are solid or perforated to form a lattice, and of plane membranes folded around these intercalated plates. These intercalated plates and membranes are introduced together into the container case which consists of the upper rigid element 62 and is closed by positioning the lower rigid element 61, the peripheral leaktightness between the compartments through which the blood passes in one case and the dialysis liquid in the other case, and around the orifices 40 and 42, being ensured by the flexible element 60, and the various elements 60, 61 and 62 having local ribs or suitable extra thicknesses. It is to be noted that the orifices 40 and 42 for the dialysis liquid open out on that face of the haemodialyser which is provided with the gasket 60, and that the orifices 12a and 13a for the blood open out on the opposite face, the latter communicating with the tubes 12 and 13, only tube 12 being visible in FIG. 5.

Figure 8:
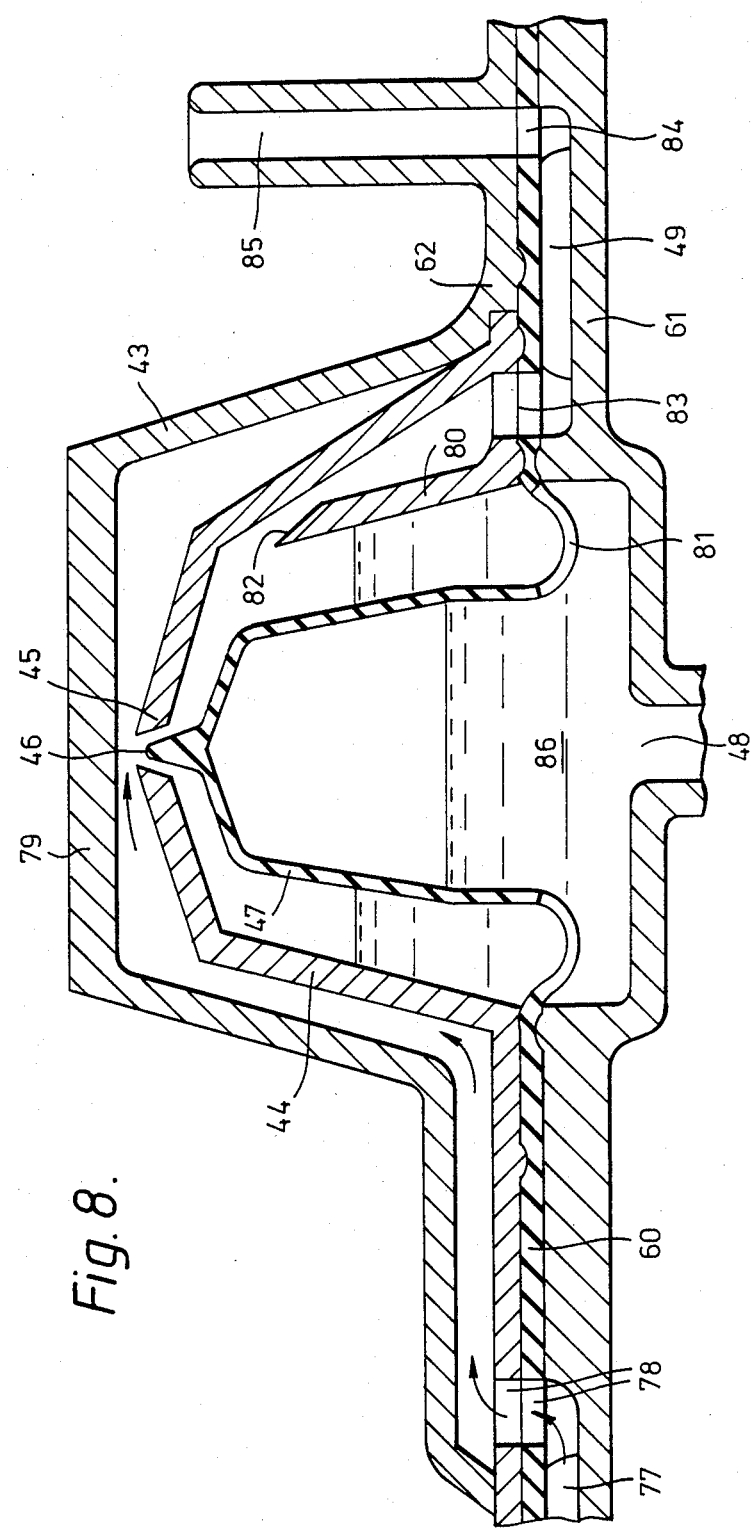
FIG. 8 is a section, taken along an axial plane, of the float-type device for regulating the pressure of the dialysis liquid, and of the tube for connecting this device to the atmosphere.

With reference to FIG. 8 in particular, the used dialysis liquid which flows from the orifice 42 between the ribs 77 passes through the flexible element 60 via the orifice 78, and flows, in the frustoconical shape 79 of the element 62, around a substantially coaxial, attached part 80 constituting part of the tank 44. The frustoconical element 79 has a side channel 43 made of a transparent material, for example polymethyl methacrylate, welded to the element 62, on either side of which cover the light-emitting and light-receiving devices constituting a colorimeter can be positioned, which colorimeter is integral with the console 10 and detects any possible leakage of blood into the dialysis liquid. Of course, the element 62 can also be made entirely of a transparent material.

The flexible element 60 locally assumes the shape of a bell which is connected by fins 81 and provided at the top with a needle-valve 46; this bell constitutes the float 47, the fins being fairly supple so as to allow the float a sufficient freedom of movement and a sufficient clearance. The needle-valve 46 engages in the seat 45 at the top of the attached part 80. The part 80 has an overflow 82 giving access, via the orifices 83 and 84 and the ribbed channel 49, to the tube 85 for opening the float-receiving chamber 86 to atmospheric pressure. The chamber 86 communicates, via the orifice 48, with the compartment 35 for storing the used dialysis liquid.

Figure 9:
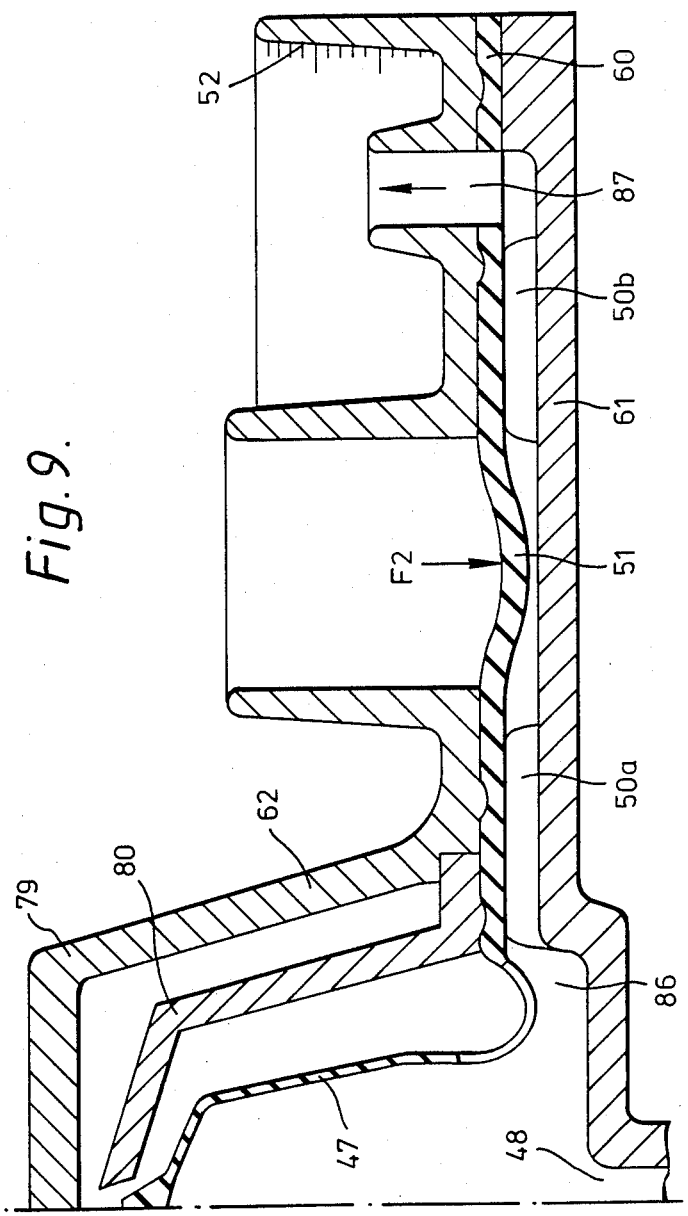
FIG. 9 is a section, taken along an axial plane, of part of the float-type device and of the means for removing and measuring amounts of liquid equal to the desired amounts of ultrafiltrate.
Figure 11:
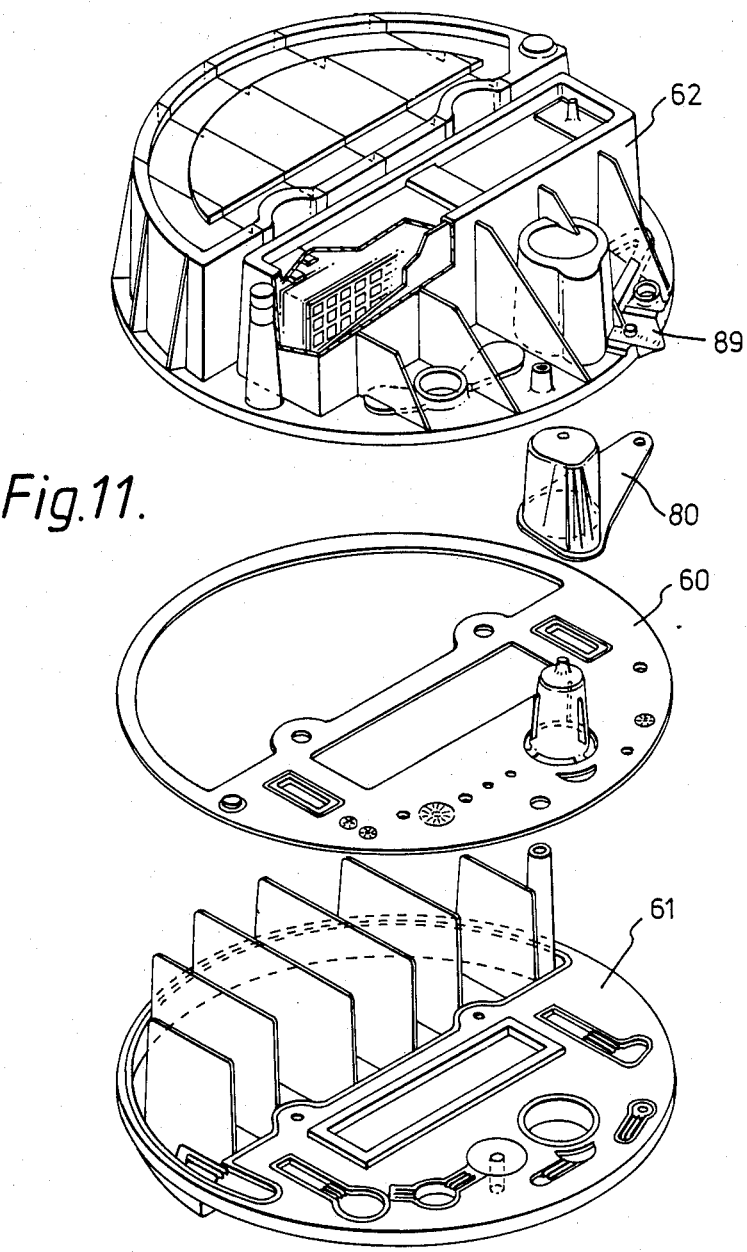
FIG. 11 is the exploded view in perspective of an integrated common unit consisting of multifunctional elements similar to the elements shown separately in FIGS. 6, 4 and 5 respectively.

If reference is now made to FIG. 9 in particular, it is seen that the ribbed channels 50a and 50b lead the dialysis liquid as far as the orifice 87, from which it can overflow into the graduated receiver 52 delimited by a peripheral wall. The capacity of the receiver 52 can be as much as 3 to 4 liters. This receiver can therefore be integrated into the common unit by being shaped, either (as shown) by the element 62, or by the element 61, which gives it the shape of a concentric ring around the common unit. In the latter case, it can be supplied by an overflow 89 [see FIG. 11].

The flow of the dialysis liquid, which takes place under gravity from the tank 44, can either be stopped, or limited and controlled, by reducing the permanent stress exerted on the deformable circular portion 51 of the gasket 60 in the direction of the arrow $F_2$, by any customary mechanical means connected, for example, to the console 10, such as a screw acting perpendicularly to the surface 51 of the gasket. The operation can be carried out continuously or, preferably, sequentially by modifying the opening time. It is also possible to replace this device by a pump similar to the membrane pump 38.

The means for storing the dialysis liquid consist, inside the container 20, of the two compartments 33 and 35 of a supple bag, each of the compartments being capable of occupying a volume equal to the internal volume of the container. These compartments are formed, for example, from an extruded tubular sleeve made of polyethylene, heat-sealed at both ends, and are connected to the corresponding orifices and tubes 32, 36 and 48.

Preferably, these storage means can be at least partially integrated into the said common unit described above, by the fact that the lower element 61 constitutes the cover 34 of the container 20. The flattened tubular sleeve then covers the lower face of the element 61. This integration can be further increased by the fact that the flattened tubular sleeve, together with the gasket 60, can advantageously be introduced between the elements 61 and 62 or around the element 62, it being possible for the appropriate orifices to be made in the gasket 60 and in at least one of the walls of the flattened tubular sleeve.

It is apparent from the above description that, with the aid of two or three accessories held in particular in the console 10 and actuating units $F_1$ and $F_2$, only three or four elements constitute a common unit which makes it possible to perform all the functions of preparation and circulation of the dialysis liquid during a haemodialysis session, and of volumetric checking of the ultrafiltrate. By integrating a supple bag into this common unit, the latter is also capable of storing the fresh and/or used dialysis liquid.

The common unit described in this way can be delivered with its supply of concentrate solution, in a sterile pack and ready to use. The user has only to arrange this unit on the container 20, connect it to the blood circuit and position the console 10.

It is completely remarkable that it is possible to perform such a large number of such varied functions with the aid of such a considerably reduced number of components. An artificial kidney with an integrated dialysis circuit has the following advantages in particular:

(a) the use of fewer components and less material, and hence a saving in terms of energy, manufacture, assembly, transportation, storage and use. In particular. the omission of the majority of the connections, the great compactness of the integrated unit and, if appropriate, the heat-insulation of the console 10 and of the container 20 essentially eliminate the heat losses during a session, and this makes it possible considerably to simply the devices for heating and for regulating the temperature of the blood, whilst at the same time preserving a very high degree of safety.

(b) the disposable use of the dialysis circuit thus becomes substantially more accessible, resulting in:

mass production lending itself well to automation, and remarkable ease of assembly, which further increases the economy, a short life, permitting the use of inexpensive materials and a substantial relaxing of the manufacturing constraints, and the omission of any sterilisation and of the accessories which are required for this purpose.

(c) rapid, simple and safe use, namely no more sterilisation, no prior connections and fewer checks to be carried out.

All these advantages are of particular value for home dialysis.

As indicated above, the present invention can form the subject of a large number of modified embodiments within the scope of those skilled in the art. A few of these modifications will be mentioned only by way of example.

Thus, the bistable boss 70 can be dispensed with; in fact, the tube 32 only opens out in a compartment 33, devoid of air beforehand, which can therefore only receive, before use, a negligible volume of concentrate solution.

The haemodialyser 16 can be of the hollow fibre type.

The float-type device can also be constructed as shown in FIG. 10. The attached part is in this case the float 47 equipped with the needle-valve 46. The chamber 44 consists of the suitably shaped, lower element 61. It is covered by the flexible element 60 provided with an opening 45 constituting the seat of the blocking device, and it is supported by radial ribs 88. The chamber 86 is connected to the atmosphere via the tubes 49 and 85.

The device for removing liquid for checking the ultrafiltration can be connected directly to the compartment 35 for receiving the used dialysis liquid.

It is possible for the supple bag to consist of only one compartment, either for the fresh dialysis liquid or for the used dialysis liquid. The container must then be equipped with sealing gaskets. It is also possible not to use a supple bag and to allow the dialysis liquid to pass directly into the container, which becomes disposable, in which case a certain mixing of the fresh and used liquids is not excluded. If appropriate, it is then possible to integrate one or more cartridges of adsorbent materials into the common unit described above.

As has already been noted it is possible to have only partial integration of the various members of the dialysis liquid circuit. Thus, solely by way of example, it is possible only to integrate the pump 38 into the haemodialyser 16, the tank of concentrate solution 30 remaining self-contained. Likewise, the container 20 could be integrated into the common unit even if only the cover 34 constitutes one of the elements of the common unit.

We claim:

1. An artificial kidney comprising:
    (a) a hemodialyzer including:
        (i) a casing separated into first and second compartments by a membrane enabling blood to be treated by dialysis and by ultrafiltration,
        (ii) first connections for introducing and removing blood to and from said hemodialyzer mounted on said first compartment,
        (iii) second connections for introducing and removing dialysis liquid to and from said hemodialyzer mounted on said second compartment,
    (b) blood circulation means external to said hemodialyzer and connected to said first connections to circulate blood through said first compartment, at an appropriate blood pressure, above atmospheric pressure,
    (c) means for storing dialysis liquid,
    (d) means for preparing dialysis liquid, connected to said storing means and connectable to a source of water,
    (e) means for circulating dialysis liquid, connected to said storing means and to said second connections, to circulate dialysis liquid from said storing means to said second compartment of the hemodialyzer and back to said storing means,
    (f) means for removing and measuring amounts of used dialysis liquid equal to a desired amount of ultrafiltrate, connected to said means for circulating dialysis liquid downstream of said hemodialyzer,
    (g) means for controlling and checking said blood circulation means, and said means for circulating dialysis liquid, and,
    (h) a common unit consisting essentially of one multifunctional, flexible sealing sheet, provided with a first face and a second face and further provided with at least one hole belonging to said means for circulating dialysis liquid, on the first face of said sealing sheet a first rigid or semi-rigid, multifunctional element provided with a part connectable to said source of water, and on the second face of said sealing sheet a second rigid or semi-rigid multifunctional element, provided with at least two ports connectable to said storing means for dialysis liquid, whereby said flexible sealing sheet is sandwiched between said first and second multifunctional elements, said common unit being disposable and providing this intrigrated means for said preparing and circulating means for dialysis liquid, said dialysis liquid circulating through said at least one hole on both sides of said flexible sealing sheet, within said first and second rigid or semi-rigid elements.

2. An artificial kidney as claimed in claim 1, wherein said hemodialyser is at least partly integrated into said common unit.

3. An artificial kidney as claimed in claim 1, wherein said dialysis liquid storing means are at least partly integrated into said common unit.

4. An artificial kidney as claimed in claim 1, wherein said removing and measuring means are at least partly integrated into said common unit.

5. An artificial kidney as claimed in claim 1, wherein said flexible sealing sheet is of a thin, generally planar shape and further comprising means defining openings thereon.

6. An artificial kidney as claimed in claim 1, wherein at least one of said first and second multifunctional elements is formed as an injection molding.

7. An artificial kidney as claimed in claim 1, wherein the first and second of said rigid or semi-rigid multifunctional elements form first and second casing part respectively for said hemodialyser.

8. An artificial kidney as claimed in claim 1 wherein said first and second rigid or semi-rigid multifunctional parts form the housing of a membrane pump to circulate said dialysis liquid through said second compartment and wherein said flexible sealing sheet includes parts forming a membrane, intake and delivery check valve members and a peripheral seal of said membrane pump.

9. An artificial kidney as claimed in claim 1, wherein said flexible sealing sheet is pierced by at least one hole in order to be able to form an active part of a regulating float-valve enabling the pressure of the dialysis liquid in the hemodialyzer to be regulated.

10. An artificial kidney as claimed in claim 1, wherein one of said rigid or semi-rigid multifunctional elements constitutes one wall of said dialysis liquid storing means.

11. An artificial kidney as claimed in claim 10, and further comprising a supple bag located in said dialysis liquid storing means, said bag being divided into two portions each capable of occupying the whole volume of said dialysis liquid storage means, said supple bag being connected in a leaktight manner to said dialysis liquid circulation means.

12. An artificial kidney as claimed in claim 11, wherein said supple bag consists of a flattened tubular sleeve covering at least one face of one of said rigid or semi-rigid multifunctional element.

13. An artificial kidney as claimed in claim 1, wherein said hemodialyser is of the plane membrane type.

14. An artificial kidney according to claim 1, wherein one circulation pump corresponding to said means for circulating the dialysis liquid is directly disposed upstream of the hemodialyser and wherein an automatic regulation device maintains within said hemodialyzer the pressure of the dialysis liquid comprised between atmospheric pressure and the blood pressure.

15. An artificial kidney as claimed in claim 1, wherein said flexible sealing sheet forms either a check valve means or a seal for a check valve means, for removing and measuring amounts of used dialysis liquid.

* * * * *